(12) United States Patent
Christensen

(10) Patent No.: US 7,750,634 B1
(45) Date of Patent: *Jul. 6, 2010

(54) METHODS AND APPARATUS FOR DETECTING ELEMENTS AND COMPOUNDS

(76) Inventor: Charles L. Christensen, 4822 S. Nancy Dr., South Ogden, UT (US) 84403

( * ) Notice: Subject to any disclaimer, the term of this patent is extended or adjusted under 35 U.S.C. 154(b) by 370 days.

This patent is subject to a terminal disclaimer.

(21) Appl. No.: 11/824,814

(22) Filed: Jul. 3, 2007

Related U.S. Application Data

(63) Continuation-in-part of application No. 11/805,414, filed on May 22, 2007.

(60) Provisional application No. 60/747,894, filed on May 22, 2006.

(51) Int. Cl.
*G01V 3/00* (2006.01)

(52) U.S. Cl. ........................ 324/309; 324/307

(58) Field of Classification Search ......... 324/300–322; 600/407–445; 436/526, 164; 340/539.12; 315/111.21; 73/579

See application file for complete search history.

(56) References Cited

U.S. PATENT DOCUMENTS

| | | | |
|---|---|---|---|
| 5,959,529 A * | 9/1999 | Kail, IV | 340/539.12 |
| 6,686,205 B1 * | 2/2004 | Schultz et al. | 506/12 |
| 6,858,436 B2 * | 2/2005 | Zenhausern et al. | 436/164 |
| 7,036,375 B2 * | 5/2006 | Nozaki | 73/579 |
| 7,279,845 B2 * | 10/2007 | Yamaguchi et al. | 315/111.21 |
| 7,364,921 B1 * | 4/2008 | Sciorra et al. | 436/526 |
| 7,420,368 B2 * | 9/2008 | Miyazaki | 324/307 |
| 2008/0129298 A1 * | 6/2008 | Vaughan et al. | 324/322 |
| 2009/0146658 A1 * | 6/2009 | McDowell et al. | 324/309 |

OTHER PUBLICATIONS

US Office Action issued Sep. 28, 2009 in co-pending U.S. Appl. No. 11/805,414.

* cited by examiner

*Primary Examiner*—Brij B Shrivastav

(57) ABSTRACT

A method is disclosed for detecting a target substance comprises sensing one or more physical properties that affect a Nuclear Magnetic Resonance (NMR) frequency of a substance, calculating an output frequency by using the one or more physical properties and an NMR frequency associated with the target substance, generating and sending an electrical signal to a detection module, the electrical signal having the calculated output frequency; receiving an indication of the location of the target substance at the detection module.

15 Claims, 16 Drawing Sheets

METHODS AND APPARATUS FOR DETECTING ELEMENTS AND COMPOUNDS

RELATED APPLICATIONS

This application is a continuation-in-part of U.S. patent application Ser. No. 11/805,414, filed May 22, 2007, for "METHOD AND APPARATUS FOR DETECTING ELEMENTS AND COMPOUNDS," which claims the benefit under 35 U.S.C. §119(e) of U.S. Provisional Patent Application No. 60/747,894, for "ELEMENT SENSOR," filed May 22, 2006. Both of the foregoing applications are fully incorporated herein by reference.

COPYRIGHT NOTICE

© 2007 H3 Tec, LLC. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

COMPUTER SOURCE CODE SUBMITTED VIA CD-ROM APPENDIX

This application includes source code submitted via a CD-ROM appendix under 37 C.F.R. 1.52(e). The total number of compact discs, including duplicates, is two (2). The names of the files on each disc, the size of each file, and the date of creation of each file is as follows:

| Filename | File Size (bytes) | creation date | time |
| --- | --- | --- | --- |
| _ldscript | 622 | 7/7/2003 | 3:45 PM |
| adc.c | 827 | 5/15/2006 | 5:50 PM |
| adc.i | 1,770 | 7/14/2006 | 12:30 PM |
| dds_lcd.prj | 4,519 | 7/14/2006 | 1:09 PM |
| functionality.c | 145,280 | 7/20/2006 | 12:31 PM |
| functionality.dsp | 3,483 | 7/20/2006 | 12:28 PM |
| functionality.dsw | 551 | 7/20/2006 | 12:31 PM |
| functionality.plg | 1,489 | 7/20/2006 | 12:31 PM |
| gain.c | 565 | 5/15/2006 | 5:50 PM |
| gain.i | 2,357 | 7/14/2006 | 12:30 PM |
| ghs_ldscript.ld | 2,117 | 7/7/2003 | 4:04 PM |
| gnu_ldscript | 622 | 7/7/2003 | 3:45 PM |
| lh79520_evb.i | 11,075 | 4/1/2002 | 11:03 AM |
| LH79520_evbmmuinit.c | 8,326 | 5/13/2006 | 5:12 PM |
| LH79520_evbmmuinit.h | 6,762 | 5/8/2006 | 11:33 PM |
| LH79520_evbmmuinit_data.c | 14,357 | 3/28/2002 | 4:37 PM |
| LH79520_mmu.i | 3,161 | 4/1/2002 | 10:38 AM |
| lh79520_sdk_boot_arm.s | 17,986 | 9/22/2003 | 2:10 PM |
| lh79520_sdk_boot_ghs.as | 18,407 | 8/11/2003 | 3:28 PM |
| lh79520_sdk_boot_gnu.asm | 20,023 | 5/19/2006 | 5:35 PM |
| logo.c | 262,801 | 6/8/2006 | 11:10 AM |
| logo.h | 494 | 6/8/2006 | 11:10 AM |
| main.asm | 69,215 | 7/14/2006 | 12:30 PM |
| main.c | 7,816 | 6/3/2006 | 1:06 PM |
| main.h | 740 | 6/2/2006 | 11:34 AM |
| main.hex | 12,949 | 7/14/2006 | 12:30 PM |
| main.i | 11,481 | 7/14/2006 | 12:30 PM |
| main.inc | 726 | 7/14/2006 | 12:30 PM |
| main.lst | 143,424 | 7/14/2006 | 12:30 PM |
| main.map | 1,999 | 7/14/2006 | 12:30 PM |
| main.rom | 29,874 | 7/14/2006 | 12:30 PM |
| main.vec | 381 | 7/14/2006 | 12:30 PM |
| main___.c | 16,843 | 7/14/2006 | 12:30 PM |
| Makefile | 1,833 | 5/14/2006 | 11:00 PM |
| read_frequency.c | 4,353 | 5/25/2006 | 5:33 PM |
| read_frequency.i | 6,701 | 7/14/2006 | 12:30 PM |
| timer.c | 2,206 | 5/9/2006 | 10:09 AM |
| touch.c | 1,565 | 6/1/2006 | 7:06 PM |
| touch.i | 3,428 | 7/14/2006 | 12:30 PM |
| touch_dds_mag_frq.c | 19,939 | 7/14/2006 | 12:56 PM |
| uart.c | 1,713 | 7/14/2006 | 12:12 PM |
| uart.i | 2,892 | 7/14/2006 | 12:30 PM |
| untitled.c | 698 | 2/14/2006 | 4:46 PM |

These files are incorporated herein by reference.

BRIEF DESCRIPTION OF THE DRAWINGS

A more particular description of the invention briefly described above will be rendered by reference to the appended figures. Understanding that these figures only provide information concerning typical embodiments of the invention and are not therefore to be considered limiting of its scope, the invention will be described and explained with additional specificity and detail through the use of the accompanying figures, in which.

DETAILED DESCRIPTION OF PREFERRED EMBODIMENTS

The embodiments of the disclosure will be best understood by reference to the drawings. It will be readily understood that the components of the present disclosure, as generally described and illustrated in the Figures herein, could be implemented in a wide variety of different configurations. Thus, the following more detailed description of particular implementations and embodiments is not intended to limit the scope of the invention.

In some cases, well-known structures, materials, or operations are not shown or described in detail. Furthermore, the described features, structures, or characteristics may be combined in any suitable manner in one or more embodiments. It will also be readily understood that the components of the embodiments as generally described and illustrated in the Figures herein could be arranged and designed in a wide variety of different configurations.

Figure 1:
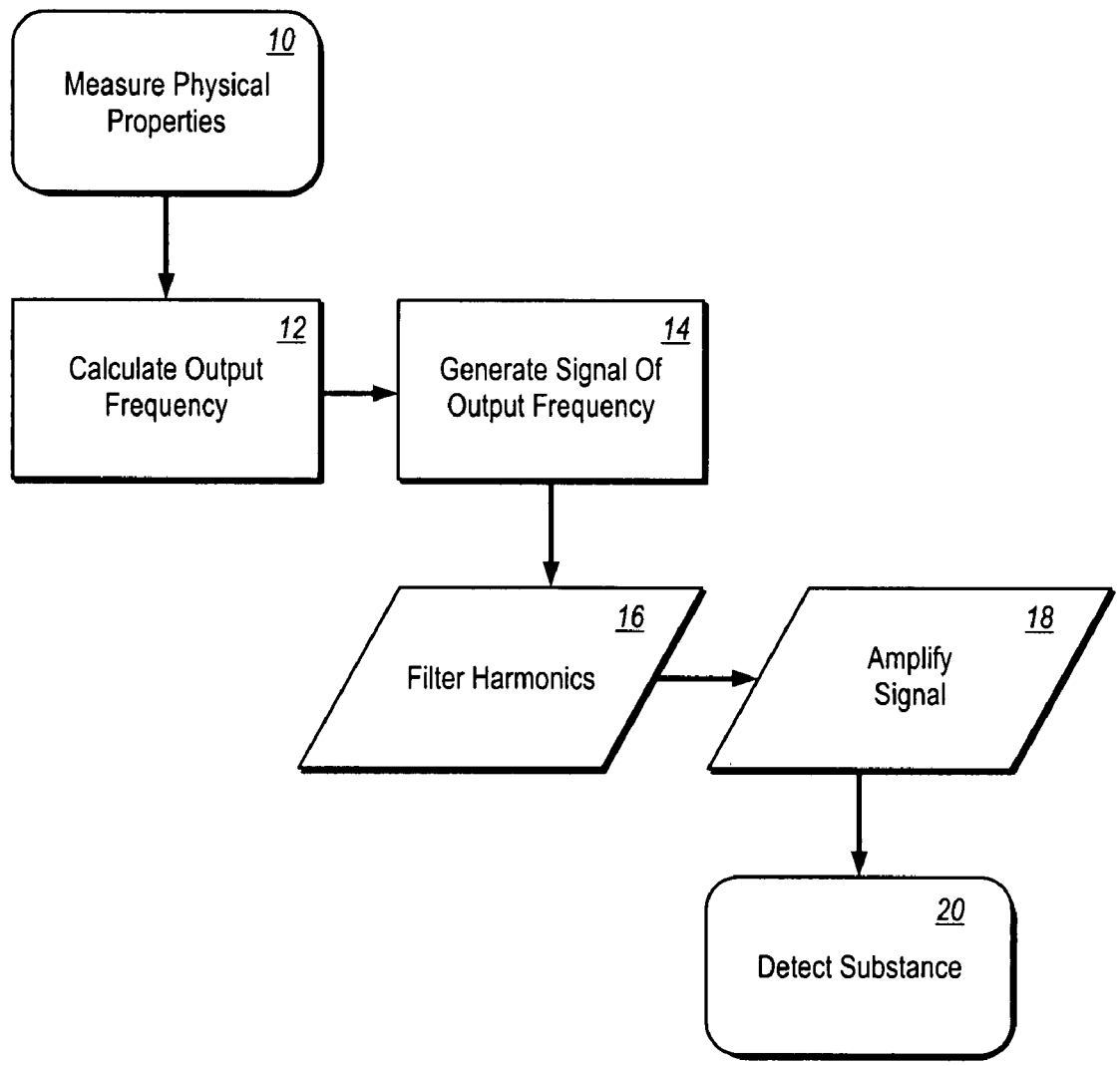
FIG. 1 shows a flow chart of one implementation of a process of detecting an element.

FIG. 1 shows a flowchart of one embodiment of a method for detecting a substance. Detecting a target substance, whether a compound or an element, may begin with 10 sensing and measuring the various physical properties that affect the Nuclear Magnetic Resonance (NMR) frequency of a substance. Every known element has a characteristic NMR frequency, which is a known constant under defined conditions. Table 1 provides the NMR frequency constants for each element.

TABLE 1

Nuclear Magnetic Resonance Frequencies for all Elements

| ELEMENT | Abbrev. | Isotope | Freq. (Hz) |
|---|---|---|---|
| Actinium | Ac | | 13.1 |
| Aluminum | Al | | 26.057 |
| Americium | Am | | 5.76 |
| Antimony | Sb | 121 | 23.93 |
| Antimony | Sb | 123 | 12.959 |
| Argon | Ar | 37 | 11.93 |
| Argon | Ar | 39 | 6.65 |
| Arsenic | As | | 11.126 |
| Barium | Ba | 135 | 9.934 |
| Barium | Ba | 137 | 236.57 |
| Berkelium | Bk | | 10.23 |
| Beryllium | Be | | 14.053 |
| Bismuth | Bi | | 16.069 |
| Boron | B | 10 | 10.746 |
| Boron | B | 11 | 32.084 |
| Bromine | Br | 79 | 25.053 |
| Bromine | Br | 81 | 27.006 |
| Cadmium | Cd | 111 | 21.205 |
| Cadmium | Cd | 113 | 22.182 |
| Calcium | Ca | | 6.728 |
| Carbon | C | | 25.144 |
| Cerium | Ce | 139 | 11.98 |
| Cerium | Ce | 141 | 4.93 |
| Cesium | Cs | | 13.117 |
| Chlorine | Cl | 35 | 9.798 |
| Chlorine | Cl | 37 | 8.156 |
| Chromium | Cr | | 5.652 |
| Cobalt | Co | | 23.614 |
| Copper | Cu | 63 | 26.505 |
| Copper | Cu | 65 | 28.394 |
| Curium | Cm | 245 | 2.558 |
| Curium | Cm | 247 | 1.472 |
| Dysprosium | Dy | 161 | 3.294 |
| Dysprosium | Dy | 163 | 4.583 |
| Einsteiniu | Es | | 20.972 |
| Erbium | Er | | 2.89 |
| Europium | Eu | 151 | 24.801 |
| Europinum | Eu | 153 | 10.951 |
| Flourine | F | | 94.077 |
| Gadolinium | Gd | 155 | 3.819 |
| Gadolinium | Gd | 157 | 4.774 |
| Gallium | Ga | 69 | 24.003 |
| Gallium | Ga | 71 | 30.495 |
| Germanium | Ge | | 3.488 |
| Gold | Au | | 1.712 |
| Hafnium | Hf | 177 | 3.12 |
| Hafnium | Hf | 179 | 1.869 |
| Helium | He | | 76.178 |
| Holimium | Ho | | 20.513 |
| Hydrogen | H | 1 | 100 |
| Hydrogen | H | 2 | 15.351 |
| Hydrogen | H | 3 | 106.663 |
| Indium | In | 113 | 21.886 |
| Indium | In | 115 | 21.914 |
| Iodine | I | | 20.007 |
| Iridium | Ir | 191 | 1.718 |
| Iridium | Ir | 193 | 1.871 |
| Iron | Fe | 0 | 3.231 |
| krypton | Kr | | 3.847 |
| Lanthanum | La | 138 | 13.193 |
| Lanthanum | La | 139 | 13.193 |
| Lead | L | | 20.921 |
| Lithium | Li | 6 | 14.716 |
| Lithium | Li | 7 | 38.863 |
| Lutetium | Lu | | 11.407 |
| Magnesium | Mg | | 6.119 |
| Manganese | Mn | | 24.664 |
| Mercury | Hg | 199 | 17.827 |
| Mercury | Hg | 201 | 6.599 |
| Molybdenum | Mo | 95 | 6.514 |
| Molybdenum | Mo | 97 | 6.652 |
| Neodymium | Nd | 143 | 5.437 |
| Neodymium | Nd | 145 | 3.346 |
| Neon | Ne | | 7.894 |
| Neptunium | Np | | 11.25 |
| Nickel | Ni | | 8.936 |
| Niobium | Nb | | 24.442 |
| Nitrogen | N | 14 | 7.224 |
| Nitrogen | N | 15 | 10.133 |
| Osmium | Os | 187 | 2.282 |
| Osmium | Os | 189 | 7.758 |
| Oxygen | O | | 13.557 |
| Palladium | Pd | | 4.576 |
| Phosphorou | P | | 40.481 |
| Platinum | Pt | | 21.499 |
| Polonium | Po | | 24.571 |
| Potassium | K | 39 | 4.667 |
| Potassium | K | 41 | 2.561 |
| Plutonium | Pu | | 3.63 |
| Praseodymi | Pr | | 29.291 |
| Promethium | Pm | | 13.51 |
| Protactini | Pa | 231 | 23.989 |
| Protactini | Pa | 232 | 36.402 |
| Protactini | Pa | 233 | 36.402 |
| Rhenium | Re | 185 | 22.513 |
| Rhenium | Re | 187 | 22.744 |
| Rhodium | Rh | | 3.172 |
| Rubidium | Rb | 85 | 9.655 |
| Rubidium | Rb | 87 | 32.721 |
| Ruthenium | Ru | 99 | 72.14 |
| Ruthenium | Ru | 101 | 4.941 |
| Samarium | Sm | 147 | 4.128 |
| Samarium | Sm | 149 | 3.289 |
| Scandium | Sc | | 24.29 |
| Selenium | Se | | 19.092 |
| Silicon | Si | | 19.865 |
| Silver | Ag | 107 | 4.046 |
| Silver | Ag | 109 | 4.652 |
| Sodium | Na | | 26.451 |
| Strontium | Sr | | 4.333 |
| Sulfur | S | | 7.67 |
| Tantalum | Ta | | 11.97 |
| Technetium | Tc | | 22.508 |
| Tellurium | Te | 123 | 26.207 |
| Tellurium | Te | 125 | 31.596 |
| Terbium | Tb | | 22.678 |
| Thorium | Th | | 1.5 |
| Thulium | Th | | 8.271 |
| Tin | Sn | 115 | 32.699 |
| Tin | Sn | 117 | 35.625 |
| Tin | Sn | 119 | 37.272 |
| Titanium | Ti | 47 | 5.637 |
| Titanium | Ti | 49 | 5.638 |
| Tungsten | W | | 4.161 |
| Uranium | U | | 1.79 |
| Vanadium | V | 50 | 9.97 |
| Vanadium | V | 51 | 26.289 |
| Xenon | Xe | 129 | 27.66 |
| Xenon | Xe | 131 | 8.199 |
| Ytterbium | Yb | 171 | 17.613 |
| Ytterbium | Yb | 173 | 4.852 |
| Yttruim | Y | | 4.899 |
| Zinc | Zn | 6.254 | |
| Zirconium | Zr | 198.61 | |

The NMR frequency varies, however, when one or more of the conditions change. For example, the Earth's magnetic field affects NMR frequency. Some of the physical properties that affect the NMR frequency may include the Earth's magnetic field, temperature, and air pressure. These physical properties can be measured at a given location such that the characteristic NMR frequency for a substance at that location can be adjusted to compensate for the varying conditions. The measurements of the physical properties can then be input to a calculation 12 that determines the proper output frequency to be communicated to a detection module for detecting the target substance. The output frequency of some embodiments of the invention may be between 2 Hz and 2 GHz.

By way of example, in an embodiment that compensates only for the Earth's magnetic field, the output frequency is calculated from the measured strength of the Earth's magnetic field, the characteristic NMR frequency (in the case of elements) or the average of the characteristic NMR frequencies of all the atoms in a single molecule of the target substance, and a correction constant. The equation for the calculation is:

$$v_{output} = \frac{v_{NMR} \times \frac{H_{Earth}}{c}}{1000} \quad \text{Eq. 1}$$

where $v_{output}$ is the output frequency measured in hertz (Hz), $v_{NMR}$ is the Nuclear Magnetic Resonance frequency for the target substance, $H_{Earth}$ is the Earth's magnetic field in gauss, and c is a correction factor having units in gauss. For example, the correct output frequency for carbon would be 535.2 Hz if Earth's magnetic field is 0.5 gauss.

$$v_{outputC} = \frac{2514400 \times \frac{.5}{2.3488}}{1000} = 535.2 Hz$$

In the above identified equation with units in Gauss and Hertz, the correction factor is 2.3488.

As further depicted in FIG. 1, after the proper output frequency is determined, an electrical signal is generated 14 having the determined output frequency. The signal may be passed through one or more high and low band pass filters 16 to filter out noise and harmonics. There are harmonics produced by the system, itself. There are also a lot of frequencies in nature made by a several different sources (e.g., radio, microwave, etc.) When the signal is set to a specific target (e.g., 145.11 Hz, the low band pass filter is set to 145.11 Hz, and the high band pass filter is set to 145.11. This insures that no other signal can pass through the receiver. When the output frequency changes due to magnetic, temperature, and/or pressure fluctuations, the band pass filters also change.

The signal strength may be increased or decreased by passing the signal through a variable gain amplifier 18. Increasing or decreasing the strength of the signal communicated to the detection module correspondingly increases or decreases the amplifier sets the grid distance or the focal field for the scan. For example, the more power that is applied, the focal point is farther away, thereby increasing or decreasing the distance at which the detection module can detect a substance.

The signal with the proper frequency and amplitude is then used to detect the target substance 20. The detection module uses the generated signal to create an excitation field and then may monitor for a corresponding elemental response coming from the target substance. Stated differently, the detection module detects a location of the target substance by detecting an reflected signature from the element returned between the generated signal and the response signal from the target substance caused by exposure to the source signal.

Figure 2:
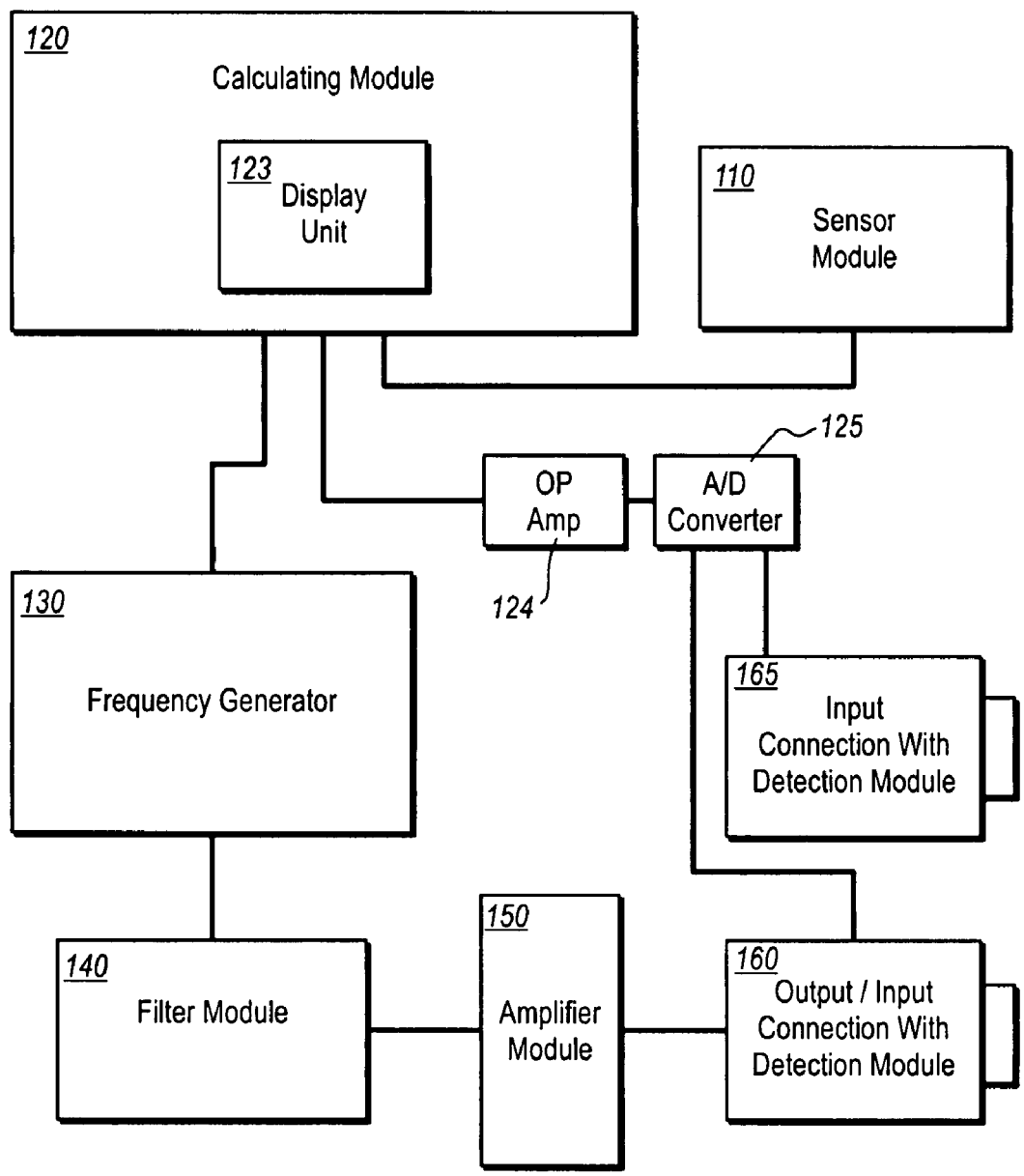
FIG. 2 shows a block diagram of one embodiment of the disclosed apparatus.

FIG. 2 depicts a block diagram of one embodiment of the disclosed apparatus, showing the interaction of different possible components. The sensor module 110 senses and measures one or more physical properties that may affect NMR frequency. For example, in one embodiment, the sensor module 110 includes a magnetometer (not shown) configured to measure a local magnetic field strength. The magnetometer may be electrically coupled to an electrical circuit for generating an electrical signal with a frequency calculated from the detected magnetic field strength. For example, the electrical circuit may include a Wheatstone bridge that produces a voltage proportional to the detected magnetic field strength. Other instruments may also be included to detect other physical properties that affect NMR frequency.

The measurements made by the sensor module 110 may be communicated to a calculating module 120, which calculates the appropriate output frequency for detecting a desired substance. The calculating module 120 may comprise a low cost, simple Digital Signal Processing (DSP) processor chip, such as an AD9850 chip in the SHARC series of chips produced by Analog Devices, Inc. The calculating component 120 may further comprise a display unit 123 adapted to allow a user to pre-select a substance to be detected, as discussed below. In one embodiment, the calculating module 120 samples the sensor module 110 and calculates the output frequency several thousand times per second, so as to maintain as nearly as possible constant compensation of varying conditions that may affect NMR of the target substance. In one embodiment, the processor takes sensor readings every 0.002 per second and makes adjustments. However, the reading frequency may be a variable in the program, that can range, for example, from 0.002 to 0.5 seconds.

In one embodiment, the magnetometer in the sensor module 110 may be sensitive to changes in ambient temperature and/or pressure. To compensate for errors caused by varying environmental conditions, according to one embodiment, the Wheatstone bridge includes temperature and/or pressure compensation. For example, the Wheatstone bridge may include one or more resistors that are sensitive to ambient temperature changes. Thus, in one embodiment, the one or more temperature sensitive resistors are configured to adjust the voltage provided by the Wheatstone bridge to counteract the errors produced in the magnetometer due to varying ambient temperatures. In addition, or in another embodiment, the Wheatstone bridge may include one or more resistor that is sensitive to pressure changes (e.g., a strain gauge on a pressure sensitive diaphragm). Thus, the voltage provided by the Wheatstone bridge may be adjusted to counteract the errors produced in the magnetometer due to varying ambient temperature and barometric pressure.

In another embodiment, the sensor module 110 may include a discrete temperature sensor and/or a discrete pressure sensor configured to adjust the signal provided by the sensor module 110 to the calculating module 120 to account for changing environmental conditions. In certain such embodiments, the calculating module 120 may be configured to analyze the signal provided by the sensor module 110 according to known or predicted temperature-resistance relationships and/or known barometric principles based on the ideal gas law. In one such embodiment, the calculating module 120 is configured to adjust the signal from the sensor module 110 based on a predetermined temperature (e.g., approximately 25 degrees Celsius) and/or a predetermined air pressure (e.g., approximately 14.7 psi) at which the sensor module 110 is calibrated for measuring nuclear magnetic resonance frequencies of target elements/isotopes. An artisan will recognize from the disclosure herein that in certain such embodiments the temperature sensor and/or the pressure sensor may be located outside the sensor module 110. For example, the temperature sensor and/or the pressure sensor may be located in the calculating module 120 to provide compensation to an unaltered signal from the sensor module 110.

The output frequency calculated by the calculating module 120 shown in FIG. 2 is then communicated to a frequency generator 130 that generates a signal having the calculated output frequency. The frequency generator may be a chip such as an AD9850-CMOS, 125 MHz Complete DDS Synthesizer manufactured by Analog Devices, or another similar chip. The generated signal (output signal) may be filtered through band pass filters in a filter module 140. The signal may be filtered through high and low band pass filters to remove any harmonics or stray signals and to clarify the signal. The amplitude of the signal may also be adjusted by passing the signal through an amplifier module 150 to increase or decrease the strength of the signal. Adjusting the strength of the signal may correspondingly increase or decrease the sensitivity of the detection module using the signal to detect a target substance.

As further depicted in FIG. 2, an embodiment may comprise more than one detection module. While a single detection module may generally be sufficient to detect a target substance, using more than one detection module may facilitate detection of a target substance through barriers. The embodiment of FIG. 2 comprises connectors for two detection modules. In this embodiment a detection module connected to connector 160 communicates the source signal, which is generated by the frequency generator. A detection module connected to connector 160 also may receive a reflected signal, which is the atomic signature of the element or compound that is set for the target. For example, if the device is set for 111.22 Hz, the atom will reflect 111.22 and nothing else. Accordingly, the system filters out all the possibilities except for 111.22. In the embodiment of FIG. 2, connector 160 may be adapted to accept input from a detection module. Input from a detection module may include an indication of detection and/or location of a target substance. Connector 165 of the embodiment in FIG. 2 may be adapted to only receive input from an associated detection module. Where an embodiment employs more than one detection module to detect a target substance, the embodiment may be adapted to alternate which of the multiple detection modules is receiving. In one embodiment, the A/D and the D/A sets the target spin, and reads for that spin. It is converted at the silicon level. To detect multiple elements or molecules, a switching algorithm may be provided that cycles through the different elements or compounds to be detected. A timing feature may also be provided that sets how fast to cycle through the list of elements/compounds. In one embodiment, the system may scan through the entire periodic table, stopping at whatever element or molecule it finds. Whether the detection module associated with connector 160 or 165 is receiving, the input may be passed through an Analog/Digital converter 125 to convert the received analog input signals to a digital signals so that they may be digitally manipulated, converted and used to display information. The input signals may also be amplified by an op-amp 124 to a level of optimum performance. In one embodiment, the input (reflected) signal is sent back through the A/D converter. It is then sent through the band pass filters. If there is a reflected signal that is equal to the target signal, the "listening" circuit is closed, and alignment occurs relative to the arm aligning to the element or compound, as discussed in greater detail below. In one embodiment, the listening circuit is part of the A/D path back to the processor. After filtering out any non-nominal signature it compares the signal to the target signal, and when they are equal, the circuit closes.

In the embodiment of FIG. 2, the calculating module 120 may further comprise a display unit 123 adapted to allow a user to pre-select a target substance to be detected. The display unit 123 may be a touch screen that allows a user to easily navigate menus by touching points on the screen, or may have other controls to allow pre-selection of a target substance. The display unit 123 may be configured to provide an initial screen having a main menu with one or more options such as 'Configuration,' 'Test,' Run,' and 'Receive.' The menu may be a drop down style menu. Upon selecting an option from the main menu, another screen corresponding to the selected main menu option may appear. The 'Configuration' screen may comprise a series of fields to specify options such as the 'Number of Elements' to be detected, the 'Number of Compounds' to be detected, and 'Timing' for switching between detection of the different elements or compounds. The 'Configuration' screen may also comprise controls, such as a set of radio buttons or other means, to select the method of detection, namely detection of an element, a compound, or both. The 'Configuration' screen may also include controls for selecting which detection module is active and controls for specifying the timing of both the interval of each read and the interval between each read performed by the detection module. The 'Configuration' screen may also include controls for specifying whether one, or more than one, detection module is to be employed in detecting the location of a target substance. Where more than one detection module is employed, the 'Configuration' screen may also include controls for selecting which detection module is providing the source signal and which detection module(s) will read input to detect the location of the target substance.

With continued reference to the display screen of the embodiment of FIG. 2, the 'Test' screen associated with the 'Test' option of the main menu may allow a user to test a current configuration. The 'Test' screen may comprise fields for selecting features to be tested and then displaying the status of the selected features and/or the results of testing the selected features. For example, the 'Test' screen may display the current measured values of physical properties being measured by the sensing component, such as magnetic field, temperature, pressure and any other measured physical properties. The 'Test' screen may also display the send status (for example at 1 Hz, 10 Hz, 100, Hz, 1000 Hz), the receive status (for example at 1 Hz, 10 Hz, 100, Hz, 1000 Hz), the waveform of the signal at the proper output frequency, the amplifier gain, and the switch timing. The switch timing is the amount of time that the target signal stays on each of the targeted elements (e.g., 0.5 seconds). For example, the time the scan would stay on carbon would be a half second before it sets to the next element on the list. The switch timing setting configures the time between checking multiple send frequencies. The 'Test' screen may further include controls for configuring a test scenario and running the test. In one embodiment, the test screen tests the functionality of the parameters of all the functionality of the device. It is a "pre run" to ensure everything is performing nominally. It takes the most critical inputs and outputs and displays them to the screen.

With continued reference to the display screen of the embodiment of FIG. 2, the 'Run' screen associated with the 'Run' option of the main menu may provide controls for the user to operate the apparatus and detect the location of the target substance. There may be separate screens for elements and compounds. The appropriate 'Run' screen (element or compound, or alternating between the two) may automatically appear according to designation of the detection method from the 'Configuration' screen. In another embodiment there may be a control for selecting either element or compound and toggling between the different 'Run' screens accordingly. The controls of a 'Run' Element screen may include a series of drop-down boxes or other means to select the target elements and/or designate the NMR frequency for particular elements. The number of drop-down boxes may correspond to the number of elements designated on the 'Configuration' screen. The controls of a 'Run' Compound screen may include a series of drop down boxes for selecting the elements of each compound. The number of compounds for which elements must be designated may correspond to the number of compounds designated on the 'Configuration screen. The controls on the 'Run' screen may also include a start button, a stop button, and a back button. Further, some embodiments may also include Macro and Micro tuning controls The tuning feature is a way of manually changing the target settings. In one embodiment, it sets macro (1.) and micro (0.1) to scan in large increments or small increments, respectively. This may be used to adjust the device to scan an unknown substance or compound until a reflection of the compound is received. Some embodiments may include indicators to show when the apparatus is sending and receiving. For example, the device may display the targeted frequency and the adjustments to the send target, and it displays the received or reflected atomic signature.

With further reference to the display screen of the embodiment of FIG. 2, the 'Receive' screen may also indicate when the apparatus is receiving the reflected atomic signature and provide additional information about the reception. For instance, the 'Receive' screen may display frequencies and buffer status for all data received within a session (up to the memory limits). Other information that may be displayed may include the channel number through which the data is being received, the timestamp or start of the transmission being received and the waveform.

Figure 3:
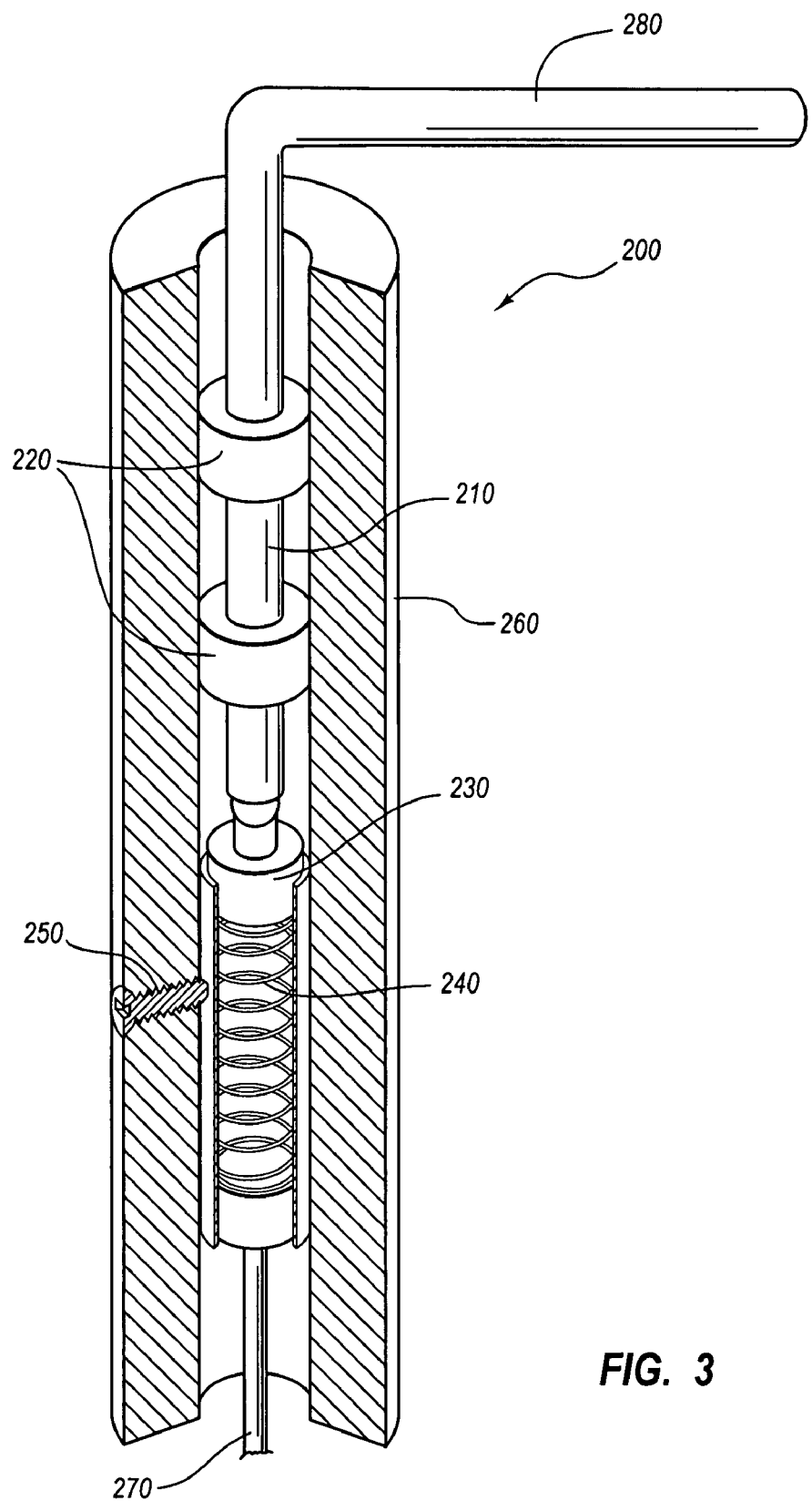
FIG. 3 shows a detection module according to one embodiment of the disclosed apparatus.
Figure 4A:
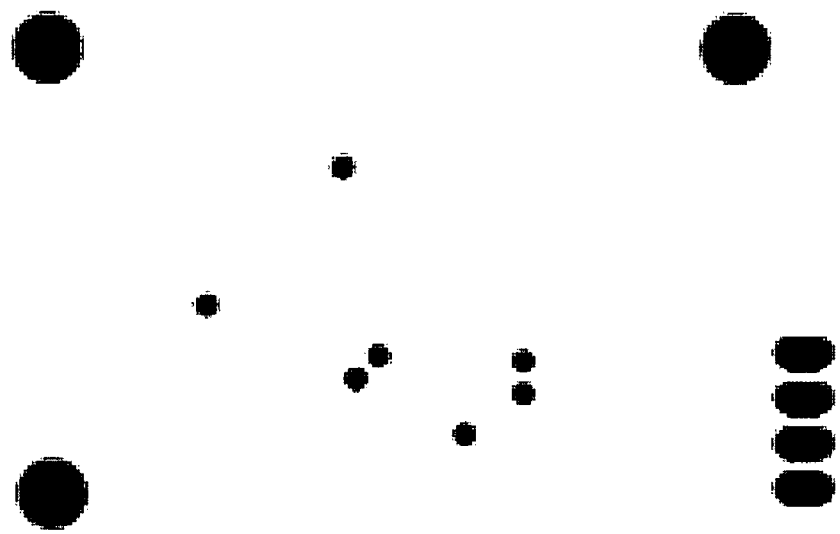
FIGS. 4A-4G depict layers of a printed circuit board (PCB) for the sensor module of FIG. 2.
Figure 4B:
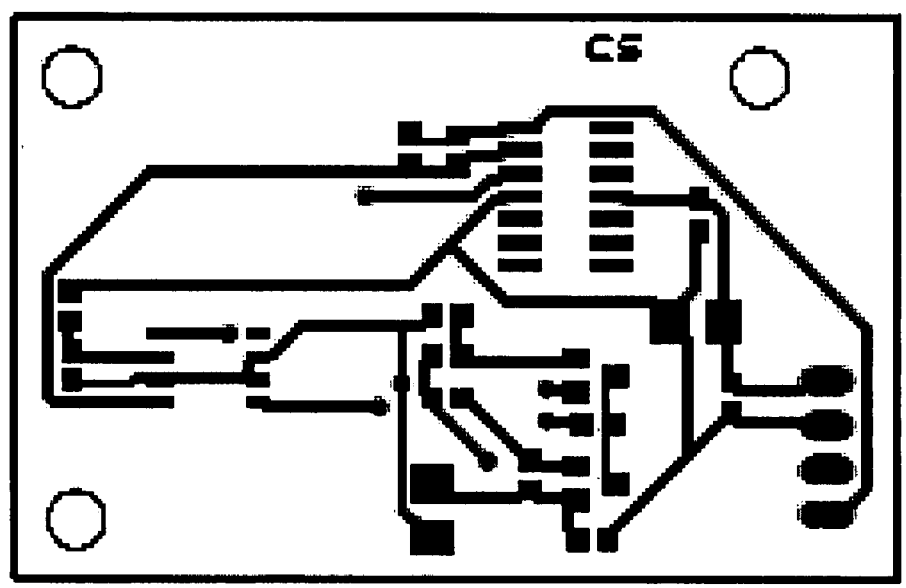
Figure 4C:
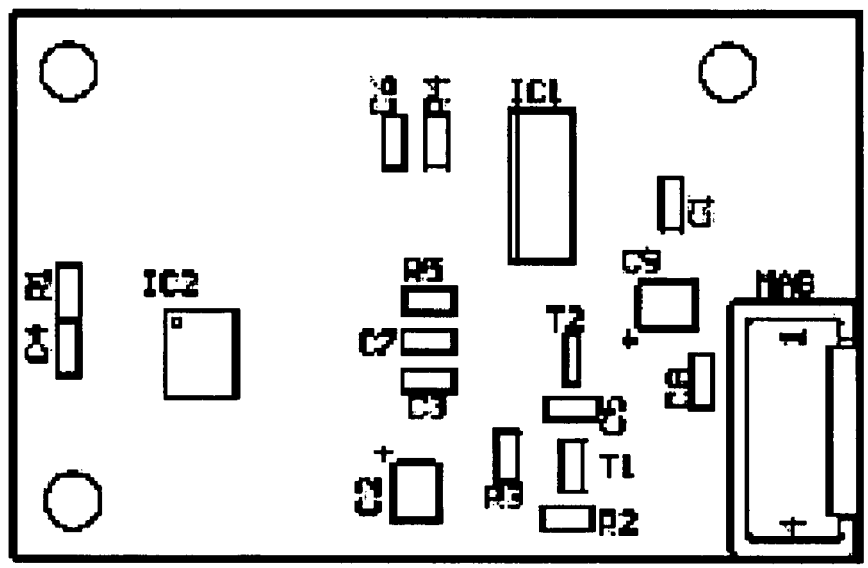
Figure 4D:
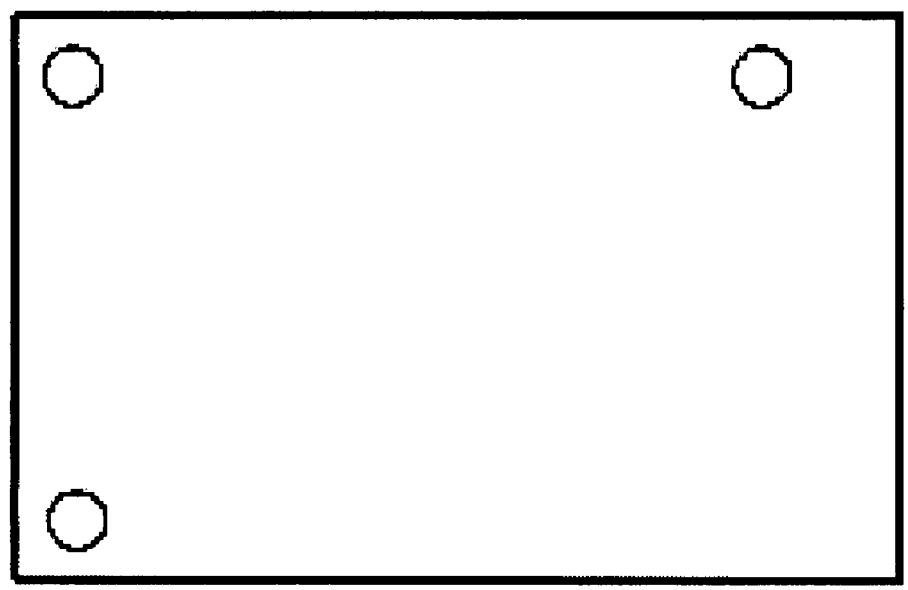
Figure 4E:
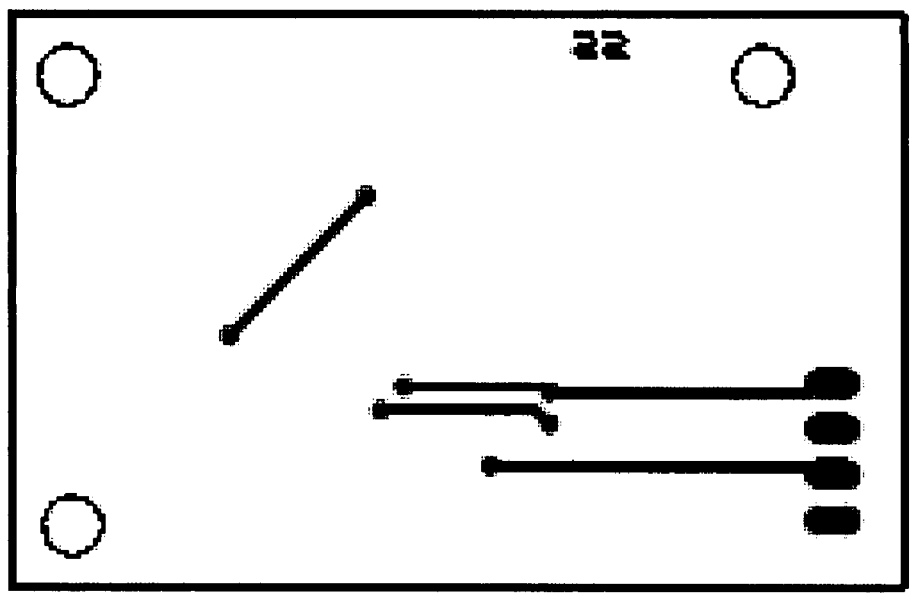
Figure 4F:
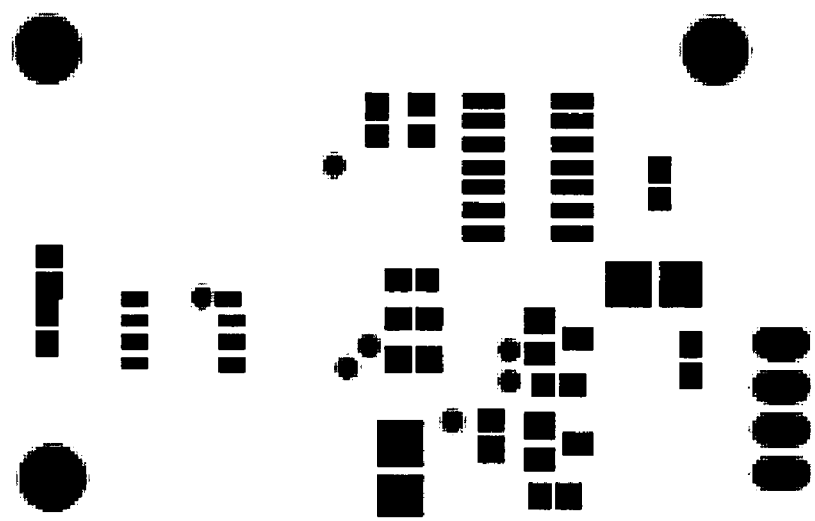
Figure 4G:
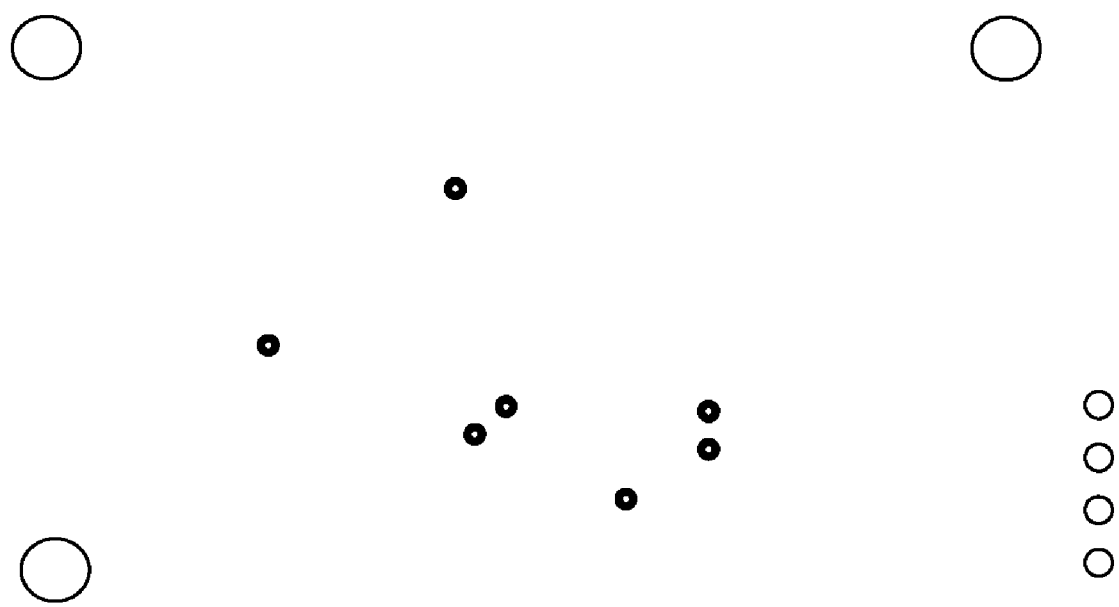
Figure 5A:
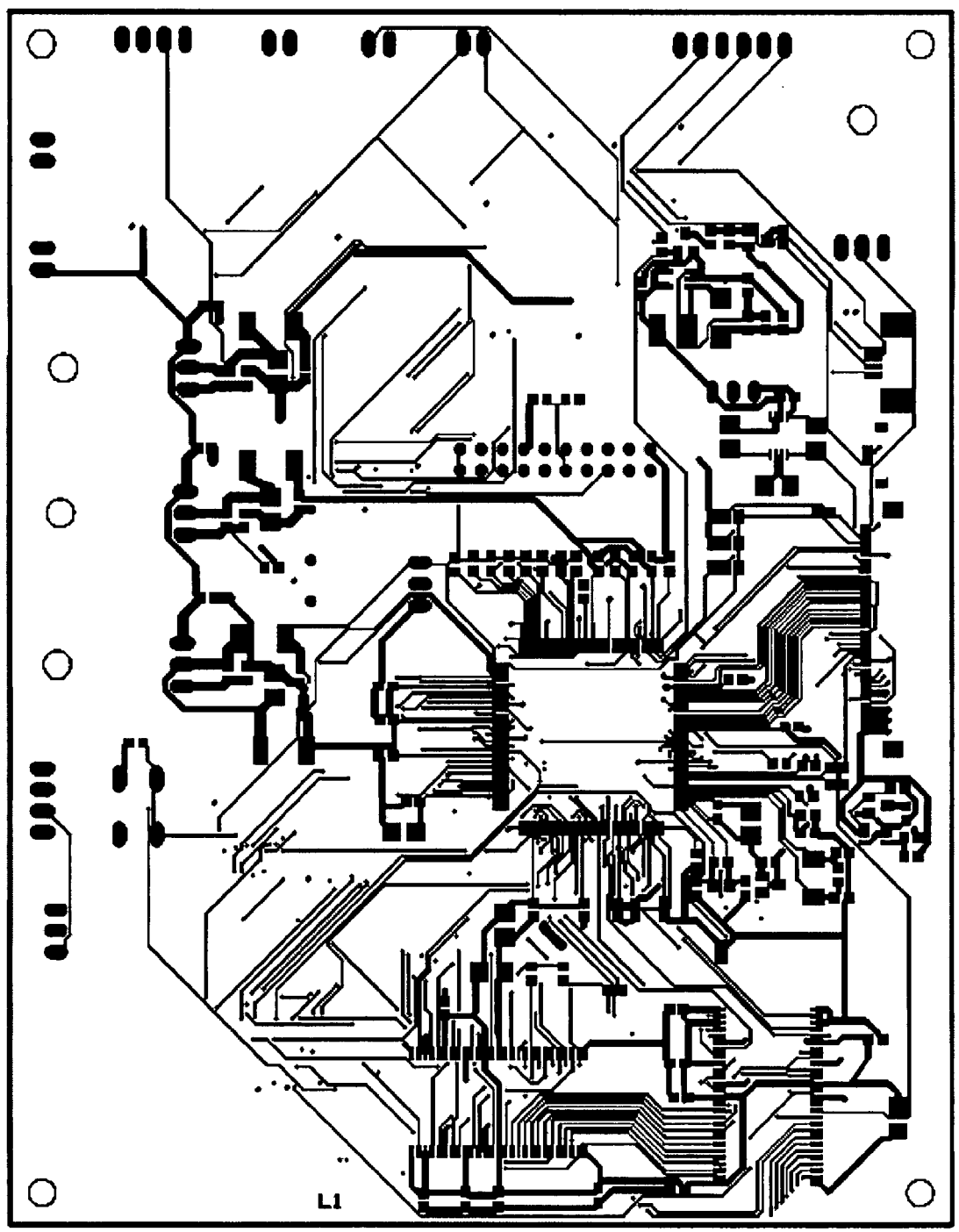
FIGS. 5A-5I depict layers of a PCB for an apparatus including the components other than the sensor module of FIG. 2.
Figure 5B:
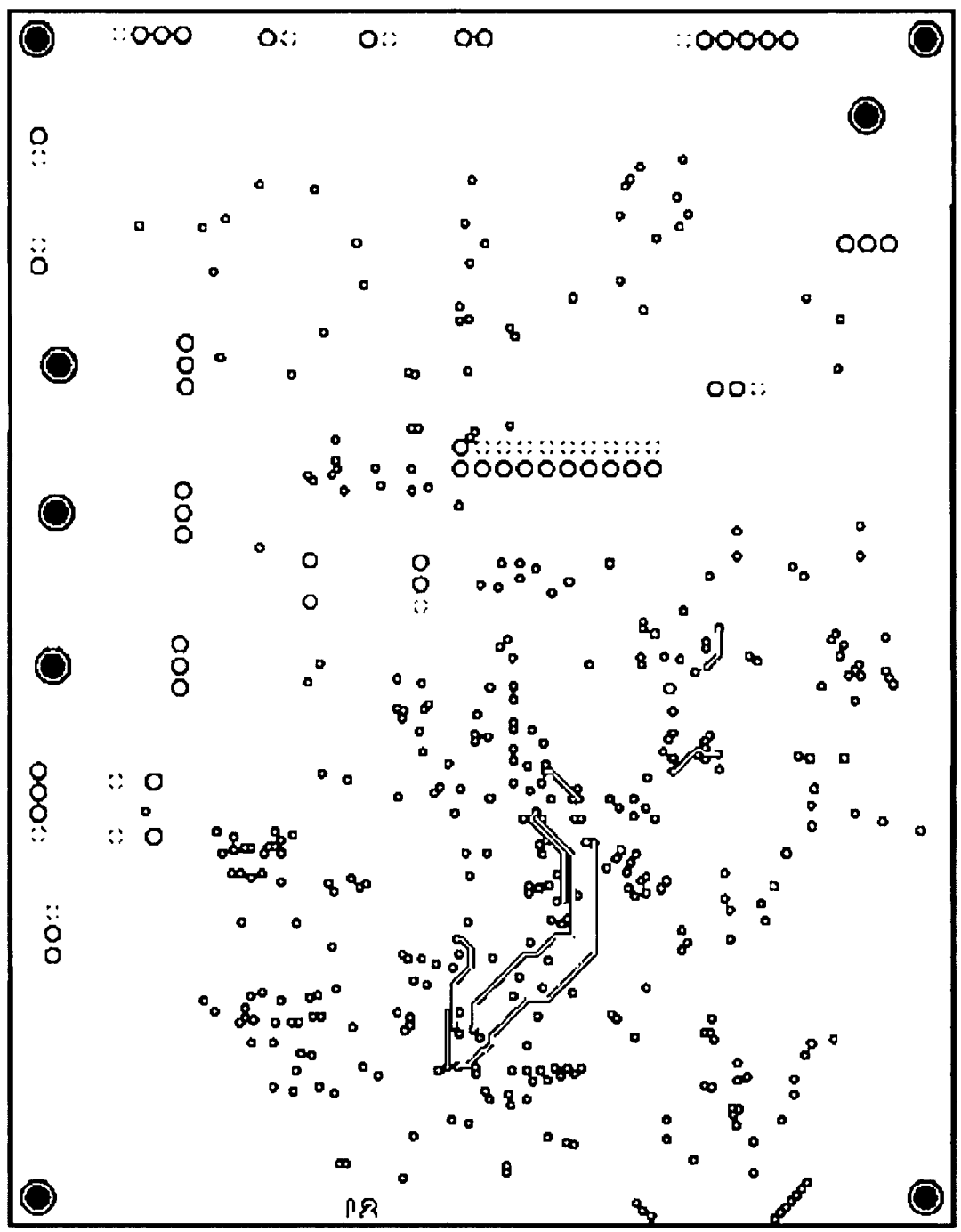
Figure 5C:
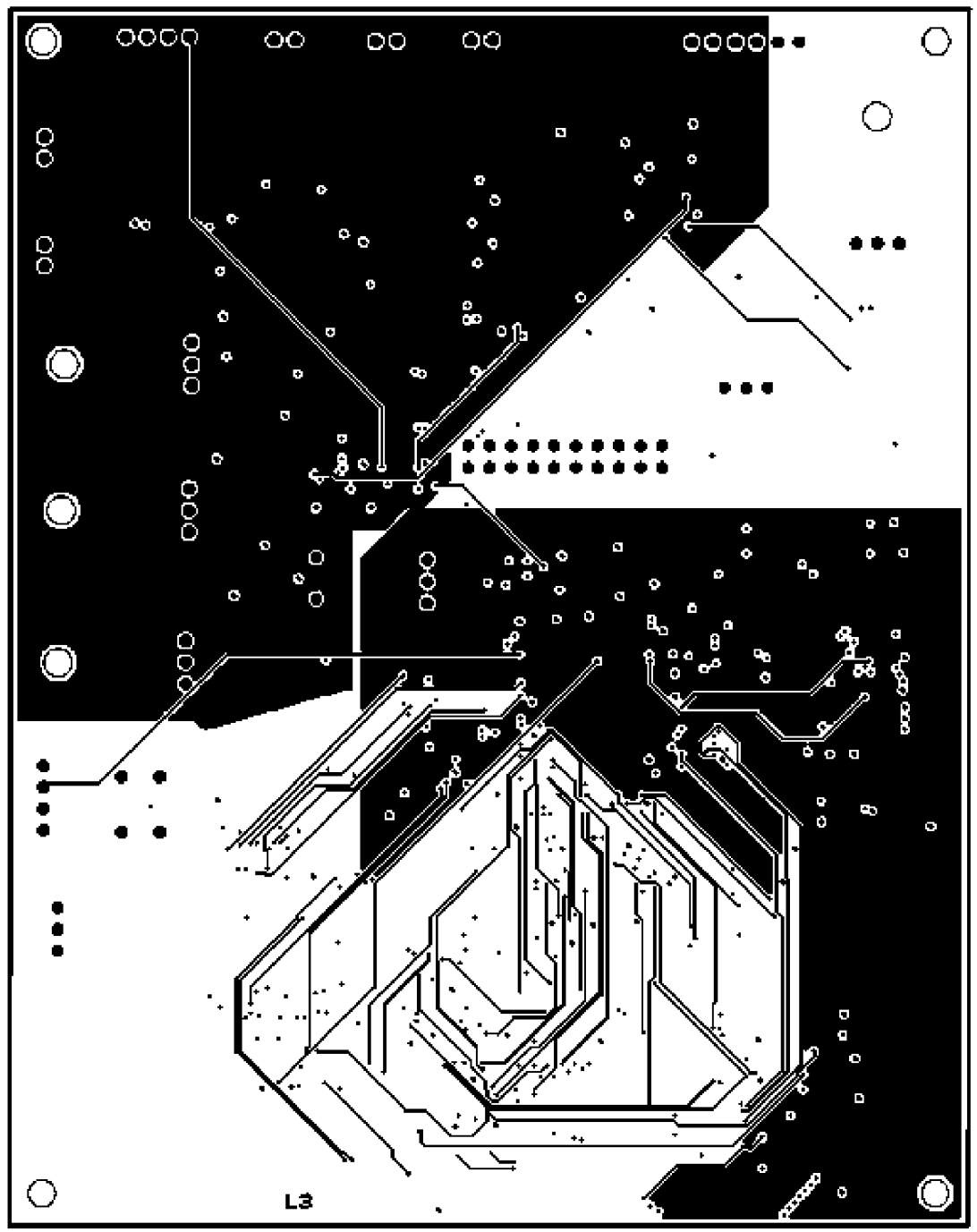
Figure 5D:
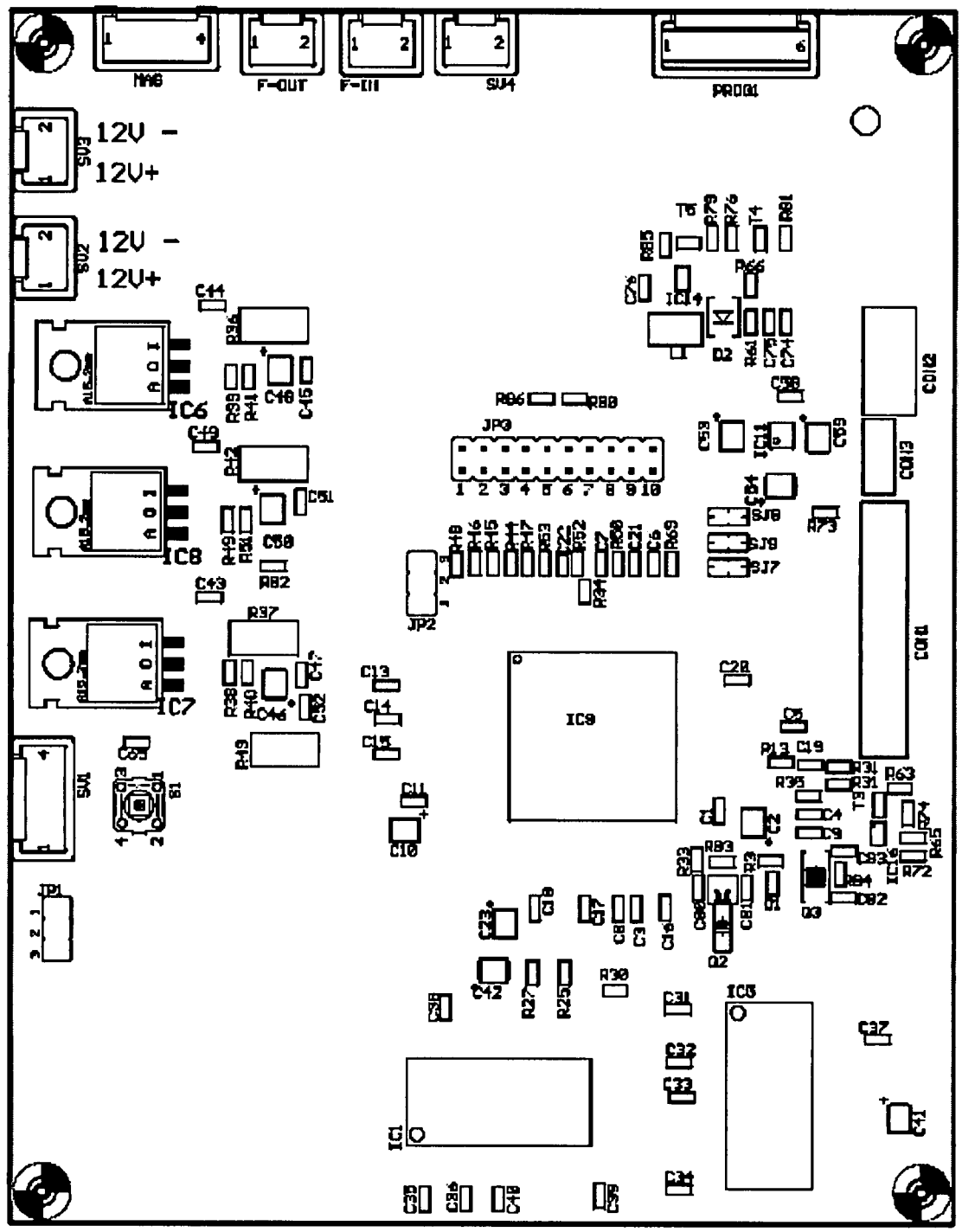
Figure 5E:
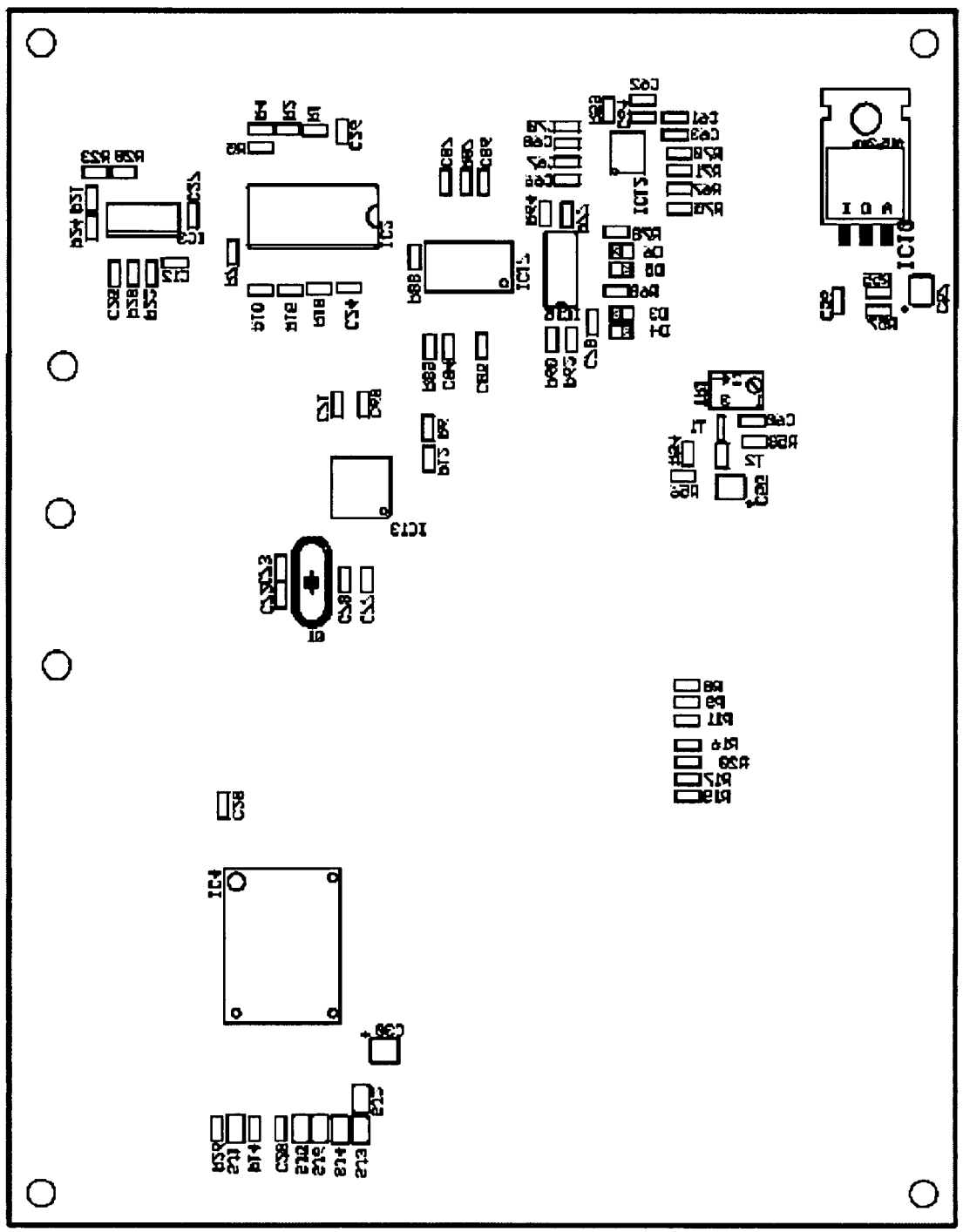
Figure 5F:
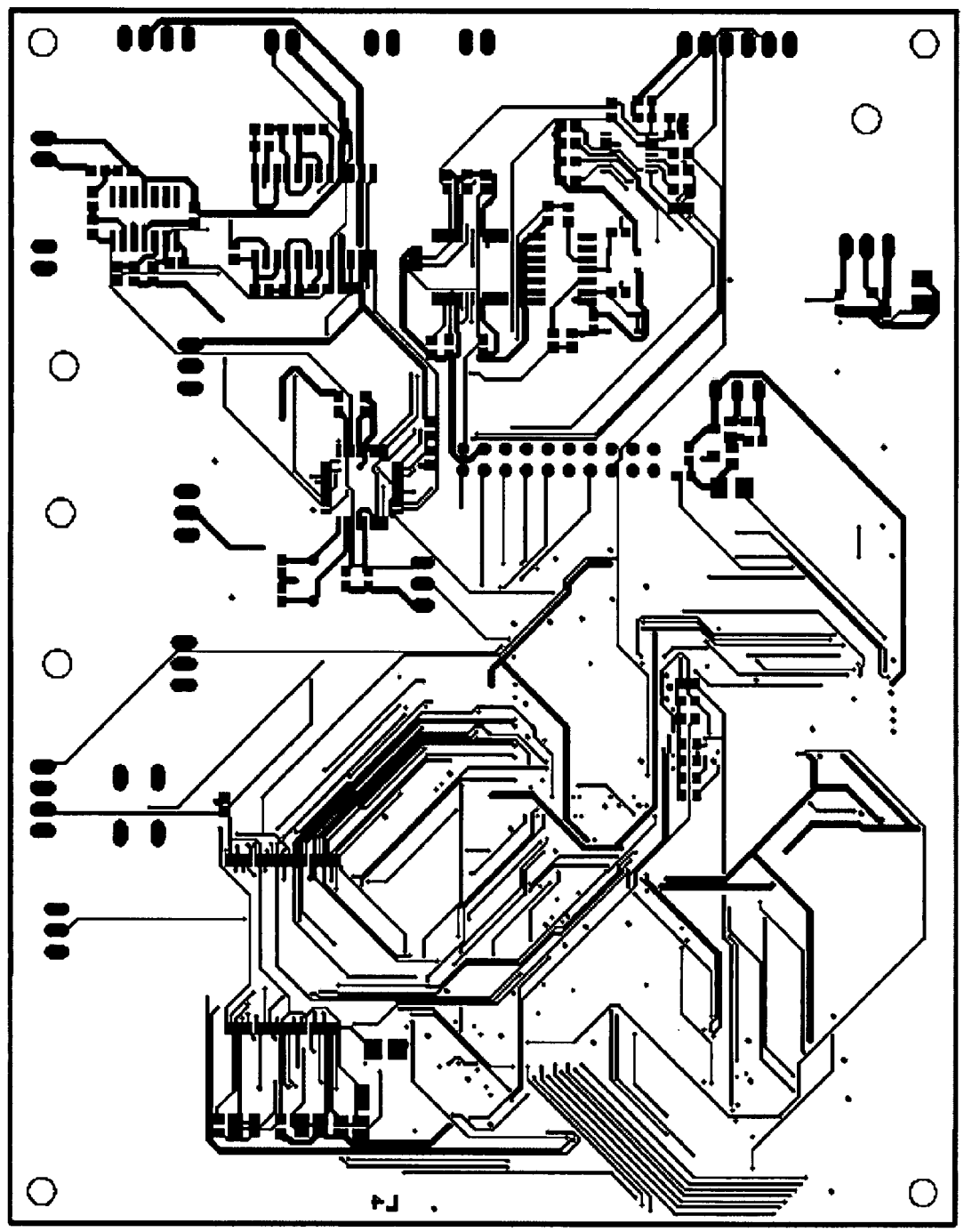
Figure 5G:
Figure 5H:
Figure 5I:
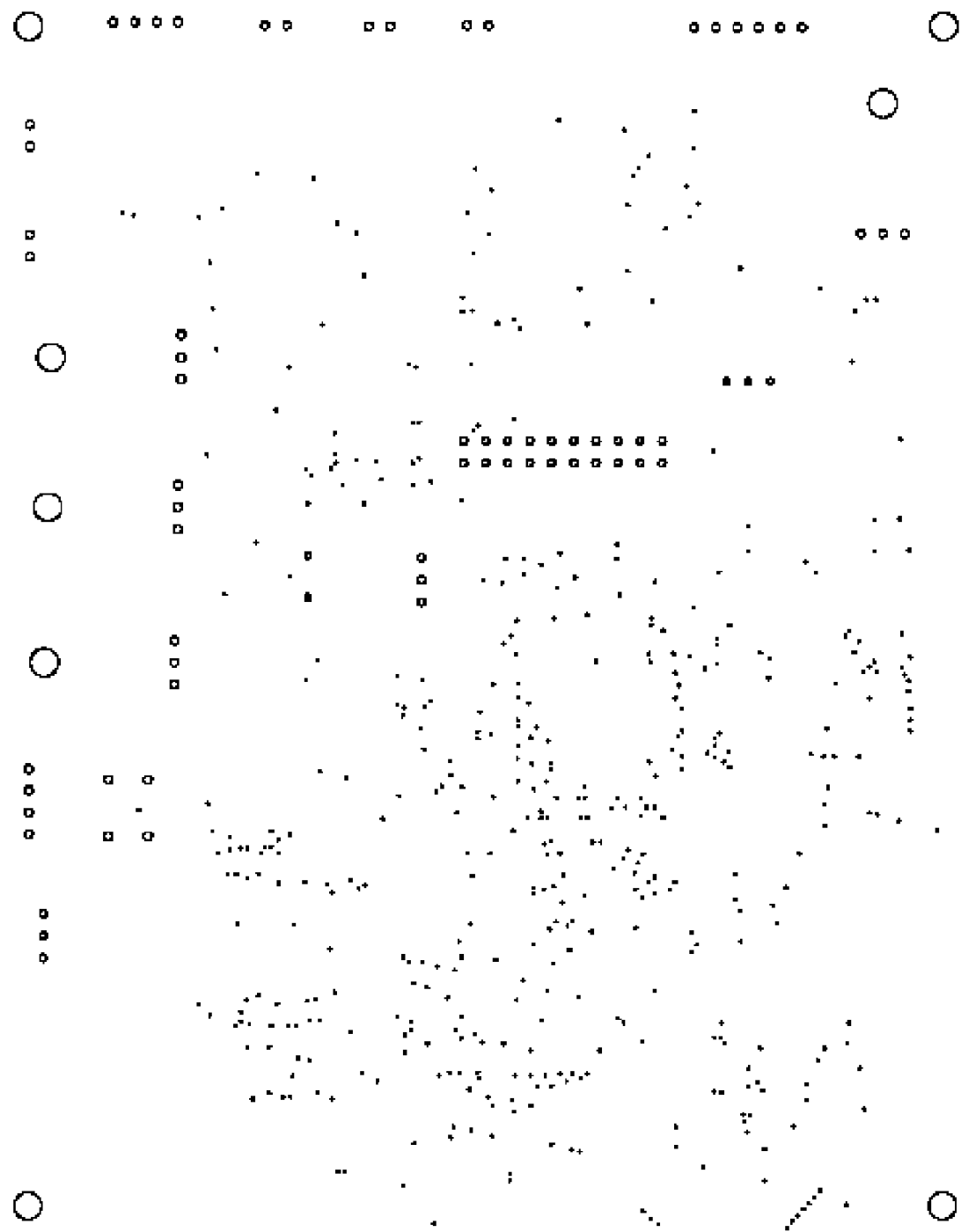

FIG. 3 depicts one embodiment of a detection module 200 having a rod 210 that pivots within a handle 260. The rod 210 is supported and allowed to swivel on precision bearings 220 inside the handle. The rod 210 may be composed of a conductive element, an electrical brush contact 230, a spring tensioner 240 for setting the pressure to insure proper contact with the rod, a set screw 250 that holds the cartridge that houses the brush, spring and connection. The embodiment of a detection module 200 locates a target substance by detecting a reflected signal generated between a generated electrical source signal and a response signal from the target substance caused by exposure to the source signal. The source signal may be communicated to the detection module 200 via a connection 270 with connector 160 (or connector 165) depicted in FIG. 2.

The embodiment of a detection module of FIG. 3 further comprises an arm 280 of the rod 210 that is configured to pivot or swivel, the rod 210 acting as an axis. In one embodiment, arm 280 can pivot 360 degrees about the axis. Similar to the rod 210, the arm 280 may be composed of a conductive material. Upon detecting the presence of the target substance, the rod 210 swivels allowing the arm 280 of the rod 210 to pivot, to point toward the location of the target substance. When pointing in the direction of the target substance, a force may be generated to pull the conductive material of the arm 280 substantially in the direction of the target substance, thereby indicating the presence and location of the target substance.

In another embodiment, two detection modules 200 are provided. Positive voltage is applied to one of the detection modules 200, while negative voltage is applied to the other detection module 200. The cycling may occur in rapid succession, e.g., 60 cycles per second. The use of two detection modules 200 and the positive/negative cycling allows for detection through solid objects, such as walls or other barriers.

In yet another embodiment of a detection module, the swiveling of a rod and pivoting of an arm may be replaced with a digital display that indicates via the display when the detection module is substantially pointed in the direction of the target substance. The user of such an embodiment would point the device in various directions until the device signals a detection of the target substances is detected, upon which continued pointing in an increasingly more constrained pattern in the direction of the continued signaling of a detection of the target substance could indicate a precise location of the target substance.

FIGS. 4A-4G depict layers of a printed circuit board (PCB) for the sensor module 110 of FIG. 2. FIGS. 5A-5H depict layers of a PCB for an apparatus including the components other than the sensor module of FIG. 2, including the calculating module 120, frequency generator 130, filter module 140, amplifier module 150, connections 160/165, A/D converter 125, and op amp 124.

A parts list detailing the components illustrated in FIGS. 4A-4G and 5A-5I is contained in Table 2.

TABLE 1

Parts List

| Qty | Value | Device | Parts |
|---|---|---|---|
| 4 | | 1N5819HW-SOD123" | D3, D4, D5, D6 |
| 1 | | 10-XX | S1 |
| 1 | | 487951-4" | CON2 |
| 1 | | B64Y | TR1 |
| 14 | | C-USC0603 | C12, C24, C25, C26, C27, C44, C45, C66, C67, C68, C70, C77, C79, C84 |
| 4 | | CPOL-USCT3528 | C48, C53, C54, C59 |
| 1 | | DIODE-SMB | D2 |
| 1 | | FH12A-50S-05H" | CON1 |
| 2 | | JP2E | JP1, JP2 |
| 1 | | JP10Q | JP3 |
| 31 | | R-US_R0603 | R1, R2, R4, R5, R6, R7, R10, R12, R14, R15, R18, R21, R22, R23, R24, R27, R28, R29, R31, R39, R41, R50, R53, R60, R62, R64, R73, R77, R85, R87, R88 |
| 5 | | S02P | F-IN, F-OUT, SV2, SV3, SV4 |
| 2 | | S04P | MAG, SV1 |
| 1 | | S06P | PROG1 |
| 6 | | SJ | SJ1, SJ2, SJ3, SJ4, SJ5, SJ6 |
| 3 | | SJ2W | SJ7, SJ8, SJ9 |
| 1 | | XF2L-0535-1" | CON3 |
| 2 | 0 5% | R-US_R0603 | R25, R30 |
| 1 | 0 ohm | R-US_R0603 | R80 |
| 2 | 0.01uF | C-USC0603 | C63, C64 |
| 1 | 0.1 pF | C-USC0603 | C17 |

TABLE 1-continued

Parts List

| Qty | Value | Device | Parts |
|---|---|---|---|
| 16 | 0.1 uF | C-USC0603 | C1, C7, C8, C9, C16, C18, C19, C20, C21, C22, C43, C47, C49, C51, C52, C65 |
| 7 | 0.1 uf | C-USC0603 | C37, C38, C39, C40, C56, C58, C60 |
| 7 | 0.1uF | C-USC0603 | C61, C62, C69, C71, C85, C86, C87 |
| 1 | 0.1uF | C-USC0603 | C78 |
| 2 | 0.1uf | C-USC0603 | C28, C29 |
| 2 | 0.05 E[1 W] | R-US_R2512 | R36, R43 |
| 2 | 0.05 E[1W] | R-US_R2512 | R37, R42 |
| 1 | 1 uF 50V | C-USC0603 | C74 |
| 1 | 1.0 M | R-US_R0603 | R84 |
| 1 | 1.1 k | R-US_R0603 | R57 |
| 1 | 2.37k 1/16 W | R-US_R0603 | R82 |
| 2 | 3.9K | R-US_R0603 | R49, R89 |
| 1 | 4.7 uf 10v | C-USC0603 | C76 |
| 1 | 8.0 MHz | HC49/S | Q1 |
| 4 | 10K | R-US_R0603 | R52, R68, R69, R78 |
| 1 | 10 M | R-US_R0603 | R83 |
| 6 | 10 k | R-US_R0603 | R26, R46, R47, R48, R66, R86 |
| 1 | 10 k 5% | R-US_R0603 | R35 |
| 4 | 10 pF | C-USC0603 | C80, C81, C82, C83 |
| 1 | 10 uH | LQH43M/N" | L1 |
| 2 | 10 uf | CPOL-USCT3528 | C55, C57 |
| 2 | 10K | R-US_R0603 | R76, R79 |
| 3 | 10k | R-US_R0603 | R44, R45, R63 |
| 2 | 10k 5% | R-US_R0603 | R32, R33 |
| 1 | 12 k | R-US_R0603 | R54 |
| 1 | 14.7456 MHz | CS10. | Q3 |
| 1 | 22 ohm | R-US_R0603 | R56 |
| 1 | 22 ohm 1/16W | R-US_R0603 | R13 |
| 1 | 22 ohm 5% | R-US_R0603 | R34 |
| 1 | 22 uF | CPOL-USCT3528 | C10 |
| 1 | 22 uF/10V | CPOL-USCT3528 | C23 |
| 1 | 22 uF/10v | CPOL-USCT3528 | C2 |
| 2 | 22 uf | CPOL-USCT3528 | C41, C42 |
| 1 | 22 uf/10v | CPOL-USCT3528 | C30 |
| 1 | 22PF 50V | C-USC0603 | C75 |
| 2 | 22 pF | C-USC0603 | C72, C73 |
| 2 | 22uF | CPOL-USCT3528 | C46, C50 |
| 1 | 32.768 kHz | 26SMD | Q2 |
| 7 | 33k 1/16W | R-US_R0603 | R8, R9, R11, R16, R17, R19, R20 |
| 1 | 74LS14D | 74LS14D | IC15 |
| 1 | 100 | R-US_R0603 | R81 |
| 1 | 100 5% | R-US_R0603 | R3 |
| 1 | 100K | R-US_R0603 | R59 |
| 1 | 100 ohm | R-US_R0603 | R55 |
| 1 | 100k | R-US_R0603 | R74 |
| 1 | 120 k | R-US_R0603 | R58 |
| 1 | 162 k | R-US_R0603 | R61 |
| 4 | 220E | R-US_R0603 | R67, R70, R71, R75 |
| 1 | 365K 1% | R-US_R0603 | R72 |
| 4 | 470 pF | C-USC0603 | C5, C6, C14, C15 |
| 1 | 470 pF | C-USC0603 | C13 |
| 2 | 576 E[1%] | R-US_R0603 | R38, R51 |
| 1 | 732K 1% | R-US_R0603 | R65 |
| 1 | 931E[1%] | R-US_R0603 | R40 |
| 9 | 10000 pF | C-USC0603 | C3, C4, C11, C31, C32, C33, C34, C35, C36 |
| 1 | AD9850BRS | AD9850" | IC17 |
| 1 | ADS7843E | ADS7843" | IC12 |
| 1 | BSS84 | BSS84 | T4 |
| 2 | BSS123 | BSS123 | T3, T5 |
| 1 | BTA54 | BAT54" | D1 |
| 1 | FMMT591ATA | BC856 | T2 |
| 1 | Flash_RC28F640J3A-120 | RC28F640J3A" | IC4 |
| 1 | LH79520LQFP | LH79520LQFP | IC9 |
| 2 | LM317S | LM317TL | IC8, IC10 |
| 1 | LM324D | LM324D | IC3 |
| 2 | LM1086CS_ADJ | LM317TL | IC6, IC7 |
| 1 | MAX335CWG | MAX335CWG | IC2 |
| 1 | MEGA88V-10AI | MEGA48A. | IC13 |
| 1 | MMBT3904 | BC846 | T1 |
| 4 | MOUNT-HOLE3.2 | MOUNT-HOLE3.2 | H1, H2, H3, H4 |
| 2 | SDRAM_MT48LC8M16A2 | MT48LC8M16A2TG-75" | IC1, IC5 |
| 1 | TPS3103K33DBVR | TPS3103" | IC16 |

TABLE 1-continued

Parts List

| Qty | Value | Device | Parts |
|---|---|---|---|
| 1 | TPS61041 | TPS61041" | IC14 |
| 1 | lm2682 | LM2682" | IC11 |

It will be obvious to those having skill in the art that many changes may be made to the details of the above-described embodiments without departing from the underlying principles of the invention.

What is claimed is:

1. A method for detecting a target substance, the method comprising:

sensing one or more physical properties that affect a Nuclear Magnetic Resonance (NMR) frequency of a substance;

calculating an output frequency by using the one or more physical properties and an NMR frequency associated with the target substance;

generating and sending an electrical signal to a detection module, the electrical signal having the calculated output frequency; and receiving an indication of the location of the target substance at the detection module, wherein receiving an indication at the detection module comprises using the generated electrical signal to produce an excitation field and then monitoring for a corresponding response from the target substance.

2. The method of claim 1, wherein the step of receiving an indication further comprises allowing an arm connected with the detection module to pivot in the direction of the substance to indicate presence of the substance.

3. The method of claim 1, wherein the step of sensing one or more physical properties comprises measuring at least one of a local strength of Earth's magnetic field, a local temperature, and a local air pressure.

4. The method of claim 1, wherein monitoring for a corresponding response further comprises detecting an interference signal generated between the generated electrical signal and the response signal from the target substance caused by exposure to the source signal.

5. The method of claim 1, wherein the output frequency is calculated using the formula $$v_{output} = \frac{v_{NMR} \times \frac{H_{Earth}}{c}}{1000}$$

where $v_{output}$ is the output frequency measured in hertz (Hz), $v_{NMR}$ is the Nuclear Magnetic Resonance frequency for the target substance, $H_{Earth}$ is the Earth's magnetic field in gauss, and c is a correction factor having units in gauss.

6. The method of claim 1, wherein the target substance is a compound and calculating the output frequency comprises averaging the NMR frequency of each atom in a molecule of the target substance to determine the NMR frequency of the substance and the output frequency is calculated using the formula $$v_{output} = \frac{v_{NMR} \times \frac{H_{Earth}}{c}}{1000}$$

where $v_{output}$ is the output frequency measured in hertz (Hz), $v_{NMR}$ is the Nuclear Magnetic Resonance frequency for the target substance, $H_{Earth}$ is the Earth's magnetic field in gauss, and c is a correction factor having units in gauss.

7. An apparatus for detecting a substance comprising:

a sensor module for measuring one or more physical properties that affect a Nuclear Magnetic Resonance (NMR) frequency of a target substance;

a calculating module for calculating an output frequency by using the one or more physical properties and an NMR frequency associated with the target substance;

a frequency generator adapted to generate an electrical signal at the output frequency calculated by the calculating component;

a first detection module for detecting the location of the target substance, wherein the first detection module detects and locates the target substance by using the generated electrical signal to produce an excitation field and then monitors for a corresponding reflected response from the target substance.

8. The apparatus of claim 7, wherein the first detection module is adapted to receive an indication of the location of the substance by pivoting a detection element about an axis towards the substance.

9. The apparatus of claim 7, wherein the sensor module comprises at least one of a magnetometer adapted to measure Earth's maximum magnetic field, a temperature sensor adapted to measure ambient air temperature, a pressure sensor adapted to measure air pressure.

10. The apparatus of claim 7 further comprising:

a filter module comprising high and low band pass filters adapted to filter harmonics from the electromagnetic signal generated by the frequency generator.

11. The apparatus of claim 7 further comprising:

an amplifier module comprising a variable gain amplifier for adjusting the amplitude of the electromagnetic signal generated by the frequency generator.

12. The apparatus of claim 7, wherein monitoring for a corresponding response further comprises detecting an interference signal generated between the generated electrical signal and the response signal from the target substance caused by exposure to the source signal.

13. The apparatus of claim 7 comprising a second detection module, wherein the first detection module is provided a positive voltage and the second detection module is provided a negative voltage.

14. The apparatus of claim 13 wherein the first and second detection modules cycle between positive and negative voltages at a specified rate.

15. The apparatus of claim 14, wherein the specified rate is 60 cycles per second.

\* \* \* \* \*